(12) United States Patent
Frison et al.

(10) Patent No.: US 7,928,254 B2
(45) Date of Patent: Apr. 19, 2011

(54) METHOD FOR PREPARING UNSATURATED FATTY HYDROXYACIDS

(75) Inventors: Natacha Frison, Creil (FR); Benoit Folleas, Senlis (FR); Jean-Louis Brayer, Nanteuil le Haudoin (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 378 days.

(21) Appl. No.: 12/083,926

(22) PCT Filed: Oct. 10, 2006

(86) PCT No.: PCT/FR2006/002268
§ 371 (c)(1),
(2), (4) Date: May 15, 2008

(87) PCT Pub. No.: WO2007/045741
PCT Pub. Date: Apr. 26, 2007

(65) Prior Publication Data
US 2008/0281114 A1   Nov. 13, 2008

(30) Foreign Application Priority Data

Oct. 21, 2005   (FR) .................................... 05 10765

(51) Int. Cl.
*C07B 37/00* (2006.01)
(52) U.S. Cl. ....................................... 554/127; 554/223
(58) Field of Classification Search .................. 554/127, 554/223
See application file for complete search history.

(56) References Cited

FOREIGN PATENT DOCUMENTS

| FR | 2 684 988 A | 6/1993 |
|----|----|----|
| JP | 63-317091 A | 12/1988 |

OTHER PUBLICATIONS

Whiteley, J.M., Methyl-substituted alpha.,-unsaturated-unsaturatedacids. III. Journal of the Chemical Society (1962) 5299-301.*
Villieras J et al., Tetrahedron Letters, vol. 26, No. 1, pp. 53-56, (1985).
Ragoussis: Synthesis, vol. 1, pp. 84-86, (1993).
List et al., Adv. Synth. Catal., vol. 347, pp. 1558-1560, (2005).
Colonge et al., Bull. Soc. Chim., pp. 551-553, (1963).
S. Dolezal et al., Collect. Czech. Chem. Commun., vol. 31, pp. 3765-3774, (1966).
Yokoi et al., Nippon Kagaku Kaishi, pp. 1415-1417, (1978).
J. Chem. Soc., pp. 5299-5301, (1962).
Swissman et al., "The Synthesis of Royal Jelly Acid and Its Homologs from Cycloalkanones," J. Org. Chem., Dec. 1964, vol. 29, pp. 3517-3520.
Lee et al., "Heterogeneous Permanganate Oxidation. 5. The Preparation of Aldehydes by Oxidative Cleavage of Carbon-Carbon Double Bonds." J. Org. Chem., 1993, vol. 58, pp. 2918-2919.
Hurd et al., "Ring-Chain Tautomerism of Hydroxy Aldehydes," J. Am. Chem. Soc., Nov. 5, 1952, vol. 74, pp. 5324-328.
Murthy et al., "Kinetics & Mechanism of Acid Bromate Oxidation of Aliphatic, Aralkyl & Alicyclic Ketones," Indian Journal of Chemistry, vol. 28A, Apr. 1989, pp. 288-291.
Plettner et al., "Why Not Be a Queen? Regioselectivity in Mandibular Secretions of Honeybee Castes," Journal of Chemical Ecology, vol. 21, No. 7, 1995, pp. 1017-1030.
Posner et al., "One-Flask, Regiospecific Conversions of Allylic Alcohols into Two-Carbon-Extended, Conjugated Dienoate Esters. Use of a New Sulfinyl Orthoester," J. Org. Chem., 1991, vol. 56, No. 25, pp. 6981-6987.
Shokyo et al., "Synthesis of (–)-Probetaenon I: Structural Confirmation of Biosynthetic Precursor of Betaenone B," J. Chem. Soc., Perkin Trans., 1990, pp. 1228-1229.
Friess, "Reactions of Per Acids. II. The Reaction of Perbenzoic Acid with Simple Cyclic Ketones. Kinetic Studies," J. Org. Chem., Jul. 1949, vol. 71, pp. 2571-2575.
Kruizinga et al., "Preparation of Macrocyclic Lactones by Ring Closure of Cesium Carboxylates," J. Am. Chem. Soc., 1981, vol. 103, No. 17, pp. 5183-5189.
Ishihara et al., "Scandium Trifluoromethanesulfonate as an Extremely Active Lewis Acid Catalyst in Acylation of Alcohols with Acid Anhydrides and Mixed Anhydrides," J. Org. Chem., 1996, vol. 61, No. 14, pp. 4560-4567.
Reagents for organic synthesis, vol. 1, Louis Fieser and Mary Fieser, p. 36 , 1967.
Introduction of a carbon chain or an aromatic ring, vol. II, Jean Mathieu and Jean Weill-Raynal, Georg Thieme Publishers, 1975, Chapter alkylidenation of methylene groups by means of aldehydes and ketones, p. 513-521.
Modein Synthetic Reaction, Second edition, Herbet O. House, Wittig-Homer reaction p. 682-709, 1972.

* cited by examiner

*Primary Examiner* — Deborah D Carr
(74) *Attorney, Agent, or Firm* — Birch, Stewart, Kolasch & Birch, LLP

(57) ABSTRACT

The invention concerns a method for preparing a compound of formula (I), wherein: $R_3$ and $R_1$ represent in particular H and n is greater than 4, said preparation method including performing a Wittig-Horner reaction with a phosphonate on a lactol, so as to obtain a hydroxyester and, optionally a saponification reaction of said hydroxyester.

12 Claims, No Drawings

METHOD FOR PREPARING UNSATURATED FATTY HYDROXYACIDS

The present invention relates to a novel method for preparing unsaturated fatty hydroxyacids. It also relates to novel unsaturated fatty hydroxyacids as well as their use, notably in the cosmetic field.

Many saturated fatty hydroxyacids are known and described in the literature for their biological properties and more particularly for their cosmetic and pharmacological properties. For example, the main lipid constituent of royal jelly from bees is an unsaturated fatty hydroxyacid, i.e. hydroxy-10-decen-2(trans)oic acid (Edward E. Smissman et al., 1964, *JOC*, 29, 3517-3520).

Different documents from the state of the art describe methods for preparing unsaturated fatty hydroxyacids and their esters (Lee et al., 1993, *J. Org. Chem.*, 58, 2918-2919; Hurd and Saunders, 1952, *J. Am. Chem. Soc.*, 74, 5324-5328; Krishnamurthy et al., 1989, Indian *J. Chem. Sect. A*, 28, 288-291; Plettner et al., 1995, *J. Chem. Ecol.*, 21, 1017-1030).

The methods already known in the state of the art, have an oxidation step during which metal salts such as chromium or manganese salts are used. Now, the use of metal salts has a certain number of drawbacks. On the one hand, as regards the products obtained by said methods, the latter may be contaminated by metal salts and therefore their cosmetic and/or pharmacological application is limited because of this contamination. On the other hand, the use of metal salts causes contamination of the environment of the industries in which the synthesis is carried out.

Other methods already known in the state of the art show that a homologation of two carbons, either by a Doebner Knoevenagel reaction, or by a Wittig reaction, on a lactol (a partially reduced lactone) of small size minoritarily leads to unsaturated hydroxyacids and majoritarily leads to tetrahydropyranylacetic or tetrahydrofuranylacetic acids (Ragoussis et al., 1993, *Synthesis*, 1, 84-86). Thus, with such methods, it is not possible to obtain unsaturated fatty hydroxyacids in satisfactory amounts.

The object of the present invention is to provide a novel method for preparing unsaturated fatty hydroxyacids, under excellent conditions, both in terms of yield but also of quality without any trace of contamination notably by cyclized products, said method may be transposed to an industrial level.

The object of the present invention is to provide a method for faster synthesis of unsaturated fatty hydroxyacids and having better yields than the methods presently used, the yield of the method of the invention being increased by 100 to 200% relatively to the methods from the state of the art.

The object of the present invention is also to provide a simplified method relatively to the methods of the state of the art, and this notably because of a reduced number of steps.

The object of the present invention is also to provide a method which does not comprise any oxidation step and which does not comprise the use of heavy metal salts, in order to avoid problems of contamination with these heavy metal salts.

Finally, the object of the present invention is to provide a method with which a whole range of products may be obtained, for which some are obtained from intermediate products unavailable commercially, but the synthesis of which is possible.

The present invention relates to a method for preparing a compound of the following formula (I):

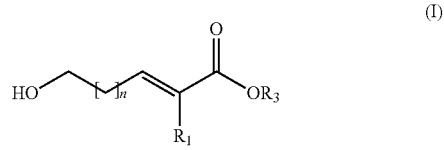

wherein:

$R_3$ represents H or a linear or branched alkyl group $R_4$ comprising 1 to 6 carbon atoms, $R_1$ represents: H, F, Cl, Br, $CF_3$ or a linear or branched alkyl group comprising from 1 to 6 carbon atoms, said alkyl group being optionally substituted with a halogen atom; and n is greater than 4, said preparation method comprising:

the application of the Wittig-Horner reaction by reacting a phosphonate of the following formula (III):

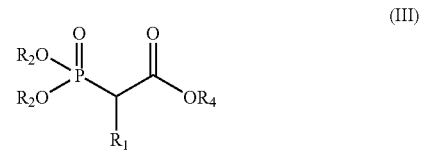

wherein:

$R_1$ is as defined above, $R_2$ represents a linear or branched alkyl group, comprising from 1 to 6 carbon atoms and preferably is a methyl or ethyl group, said $R_2$ groups may form a cycle with the oxygen atoms of the $OR_2$ groups and the phosphorus atom of the P=O group, and $R_4$ represents a linear or branched alkyl group, comprising from 1 to 6 carbon atoms, and preferably is an ethyl group, or, when $R_1$=H, the application of the Doebner-Knoevenagel reaction by reacting a malonic acid derivative of formula $R_3OOC—CH_2—COOR_3$, $R_3$ being as defined above, on a lactol of the following formula (II):

n being as defined above, in order to obtain a hydroxyester of the following formula (IV):

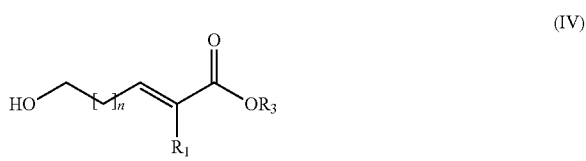

wherein n, $R_3$ and $R_1$ are as defined above, and optionally, when $R_3$ represents a group $R_4$ as defined above, a reaction for saponifying the hydroxyester of the aforementioned formula (IV) in order to obtain a hydroxyacid of the following formula (I-1):

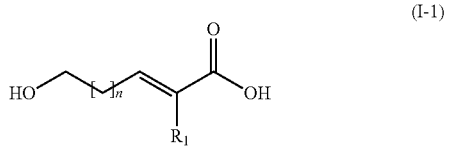
(I-1)

wherein n and $R_1$ are as defined above.

The compounds of the aforementioned formula (I) encompass the compounds of formula (IV) and the compounds of formula (I-1). Thus, the compounds of formula (IV) as defined above, correspond to compounds of formula (I) wherein $R_3$ represents a hydrogen atom or an alkyl group $R_4$ as defined above, and the compounds of formula (I-1) as defined above, correspond to compounds of formula (I) wherein $R_3$ represents a hydrogen atom.

The Wittig-Horner reaction is a reaction described in the document, Modern Synthetic Reaction, Second edition, Herbet O. House, Wittig-Horner reaction p. 682-709, and any experimental condition described in the state of the art may be used within the scope of the present invention. As an example, the Wittig-Horner reaction may be carried out in the presence of triethylphosphonoacetate and of potassium carbonate in an aqueous medium. In the latter case, the acid is directly obtained without any additional hydrolysis (References: Introduction of a carbon chain or an aromatic ring, Vol II, Jean Mathieu and Jean Weill-Raynal, Georg Thieme Publishers, 1975, Chapter: "alkylidenation of methylene groups by means of aldehydes and ketones, p. 513-521).

The present invention relates to a method for preparing a compound of the following formula (I-bis):

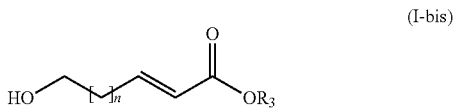
(I-bis)

wherein:
$R_3$ represents H or a linear or branched alkyl group $R_4$, comprising from 1 to 6 carbon atoms, and
n is greater than 4,
said preparation method comprising:
the application of the Wittig-Horner reaction by reacting a phosphonate of the following formula (III-bis):

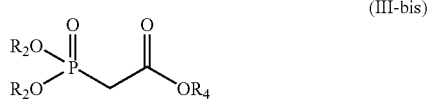
(III-bis)

wherein:
$R_2$ represents a linear or branched alkyl group, comprising from 1 to 6 carbon atoms and preferably is an ethyl or methyl group, said $R_2$ groups may form a cycle with the oxygen atoms of the $OR_2$ groups and the phosphorus atom of the P=O group, and $R_4$ represents a linear or branched alkyl group, comprising from 1 to 6 carbon atoms, and is preferably an ethyl group,
on a lactol of the following formula (II):

(II)

n being as defined above,
in order to obtain a hydroxyester of the following formula (IV-bis):

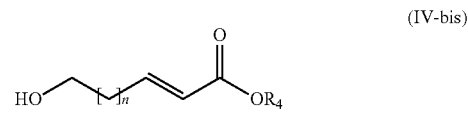
(IV-bis)

wherein n and $R_4$ are as defined above,
and, optionally a reaction for saponifying the hydroxyester of the aforementioned formula (IV-bis), in order to obtain a hydroxyacid of the following formula (I-1-bis):

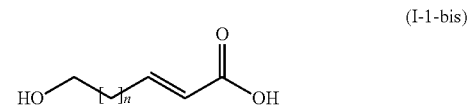
(I-1-bis)

wherein n is as defined above.

The present invention relates to a method for preparing a compound of the following formula (I-bis):

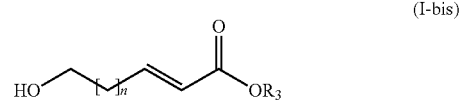
(I-bis)

wherein:
$R_3$ represents H or a linear or branched alkyl group $R_4$ comprising from 1 to 6 carbon atoms,
n is greater than 4,
said preparation method comprising:
the application of the Doebner-Knoevenagel reaction by reacting a malonic acid derivative of formula $R_3OOC$—$CH_2$—$COOR_3$, $R_3$ being as defined above, on a lactol of the following formula (II):

(II)

n being as defined above, in order to obtain a hydroxyester of the following formula (IV-bis):

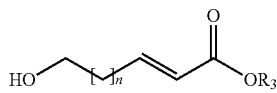

(IV-bis)

wherein n and $R_3$ are as defined above, and optionally, when $R_3$ represents a group $R_4$ as defined above, a reaction for saponifying the hydroxyester of the aforementioned formula (IV-bis), in order to obtain a hydroxyacid of the following formula (I-1-bis):

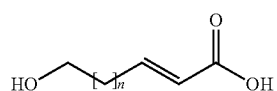

(I-1-bis)

wherein n is as defined above.

The present invention relates to a method for preparing a compound of the following formula (I-ter):

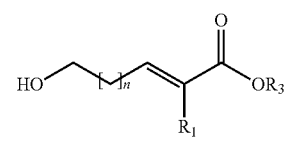

(I-ter)

wherein:

$R_3$ represents H or a linear or branched alkyl group $R_4$ comprising from 1 to 6 carbon atoms, $R_1$ represents: F, Cl, Br, $CF_3$ or a linear or branched alkyl group comprising from 1 to 6 carbon atoms, said alkyl group being optionally substituted with a halogen atom; and n is greater than 4, said preparation method comprising:

the application of the Wittig-Horner reaction by reacting a phosphonate of the following formula (III-ter):

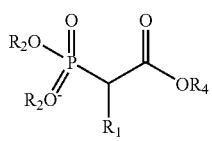

wherein:

$R_1$ is as defined above, $R_2$ represents a linear or branched alkyl group comprising from 1 to 6 carbon atoms and preferably is an ethyl or methyl group, said groups $R_2$ may form a cycle with the oxygen atoms of the $OR_2$ groups and the phosphorus atoms of the P=O group, and $R_4$ represents a linear or branched alkyl group comprising from 1 to 6 carbon atoms, and preferably is an ethyl group, on a lactol of the following formula (II):

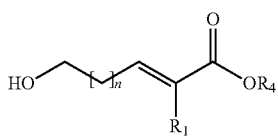

(II)

n being as defined above, in order to obtain a hydroxyester of the following formula (IV-ter):

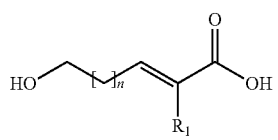

(IV-ter)

wherein n, $R_1$ and $R_4$ are as defined above, and, optionally a reaction for saponifying the hydroxyester of the aforementioned formula (IV-ter), in order to obtain a hydroxyacid of the following formula (I-1-ter):

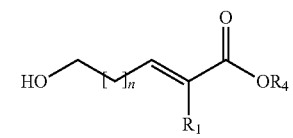

(I-1-ter)

wherein n and $R_1$ are as defined above.

The present invention also relates to a method for preparing a compound of the following formula (IV):

(IV)

wherein:

$R_4$ represents a linear or branched alkyl group, comprising from 1 to 6 carbon atoms, $R_1$ represents: H, F, Cl, Br, $CF_3$ or a linear or branched alkyl group comprising from 1 to 6 carbon atoms, said alkyl group being optionally substituted with a halogen atom; and n is greater than 4, said preparation method comprising:

the application of the Wittig-Horner reaction by reacting a phosphonate of the following formula (III):

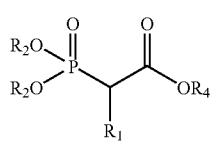

(III)

wherein:

$R_1$ is as defined above, $R_2$ represents a linear or branched alkyl group, comprising from 1 to 6 carbon atoms, and preferably is an ethyl or methyl group, said $R_2$ groups may form a cycle with the oxygen atoms of the $OR_2$ groups and the phosphorus atom of the P=O group, and $R_4$ represents a linear or branched alkyl group comprising from 1 to 6 carbon atoms, and preferably is an ethyl group, or, when $R_1$=H, the application of the Doebner-Knoevenagel reaction by reacting a malonic acid derivative of formula $R_4OOC$—$CH_2$—$COOR_4$, $R_4$ being as defined above, on a lactol of the following formula (II):

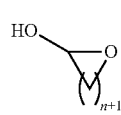

(II)

n being as defined above, in order to obtain a hydroxyester of the following formula (IV):

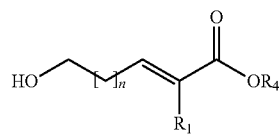

(IV)

wherein n, $R_1$ and $R_4$ are as defined above.

The present invention also relates to a method for preparing a compound of the following formula (I-1):

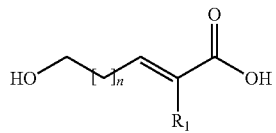

(I-1)

wherein:

$R_1$ represents: H, F, Cl, Br, $CF_3$ or a linear or branched alkyl group comprising from 1 to 6 carbon atoms, said alkyl group being optionally substituted with a halogen atom; and n is greater than 4, said preparation method comprising:

the application of the Wittig-Horner reaction by reacting a phosphonate of the following formula (III):

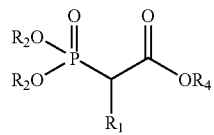

(III)

wherein:

$R_1$ is as defined above, $R_2$ represents a linear or branched alkyl group, comprising from 1 to 6 carbon atoms, and preferably is an ethyl or methyl group, said $R_2$ groups may form a cycle with the oxygen atoms of the $OR_2$ groups and the phosphorus atom of the P=O group, and $R_4$ represents a linear or branched alkyl group comprising from 1 to 6 carbon atoms, and preferably is an ethyl group, or, when $R_1$=H, the application of the Doebner-Knoevenagel reaction by reacting a malonic acid derivative of formula $R_4OOC$—$CH_2$—$COOR_4$, $R_4$ being as defined above, on a lactol of the following formula (II):

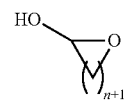

(II)

n being as defined above, in order to obtain a hydroxyester of the following formula (IV):

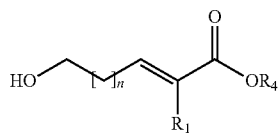

(IV)

wherein n, $R_1$ and $R_4$ are as defined above.

and a reaction for saponifying the hydroxyester of the aforementioned formula (IV), in order to obtain a hydroxyacid of the following formula (I-1):

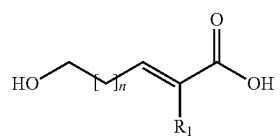

(I-1)

wherein n and $R_1$ are as defined above.

The present invention also relates to a method for preparing a compound of the following formula (I-1):

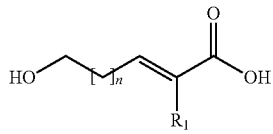

(I-1)

wherein:
R$_1$ represents: H, F, Cl, Br, CF$_3$ or a linear or branched alkyl group comprising from 1 to 6 carbon atoms, said alkyl group being optionally substituted with a halogen atom; and
n is greater than 4,
said preparation method comprising:
the application of the Doebner-Knoevenagel reaction by reacting malonic acid of formula HOOC—CH$_2$—COOH,
on a lactol of the following formula (II):

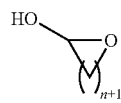

(II)

n being as defined above,
in order to obtain a hydroxyacid of the following formula (I-1):

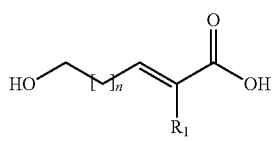

(I-1)

wherein n and R$_1$ are as defined above.
The present invention also relates to a method for preparing a compound of the following formula (I-1-bis):

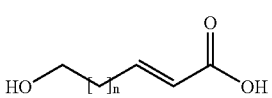

(I-1-bis)

wherein n is greater than 4,
said preparation method comprising:
the application of the Wittig-Horner reaction by reacting a phosphonate of the following formula (III-bis):

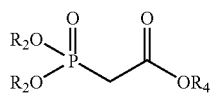

(III-bis)

wherein:
R$_2$ represents a linear or branched alkyl group, comprising from 1 to 6 carbon atoms, and preferably is an ethyl or methyl group, said R$_2$ groups may form a cycle with the oxygen atoms of the OR$_2$ groups and the phosphorus atom of the P=O group, and
R$_4$ represents a linear or branched alkyl group comprising from 1 to 6 carbon atoms, and preferably is an ethyl group,
on a lactol of the following formula (II):

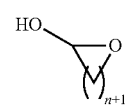

(II)

n being as defined above,
in order to obtain a hydroxyester of the following formula (IV-bis):

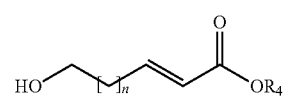

(IV-bis)

wherein n and R$_4$ are as defined above.
and a reaction for saponifying the hydroxyester of the aforementioned formula (IV-bis), in order to obtain a hydroxyacid of the following formula (I-1-bis):

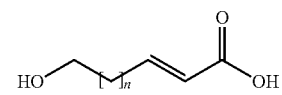

(I-1-bis)

wherein n is as defined above.
The present invention also relates to a method for preparing a compound of the following formula (I-1-bis):

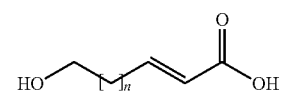

(I-1-bis)

wherein n is greater than 4,
said preparation method comprising:
the application of the Doebner-Knoevenagel reaction by reacting a malonic acid derivative of formula R$_4$OOC—CH$_2$—COOR$_4$, R$_4$ being as defined above, on a lactol of the following formula (II):

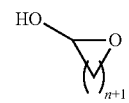

(II)

n being as defined above, in order to obtain a hydroxyester of the following formula (IV-bis):

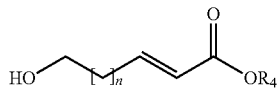
(IV-bis)

wherein n and $R_4$ are as defined above.

and a reaction for saponifying the hydroxyester of the aforementioned formula (IV-bis), in order to obtain a hydroxyacid of the following formula (I-1-bis):

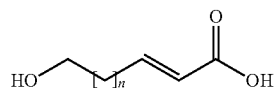
(I-1-bis)

wherein n is as defined above,

The present invention also relates to a method for preparing a compound of the following formula (I-1-bis):

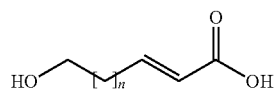
(I-1-bis)

wherein n is greater than 4, said preparation method comprising:

the application of the Doebner-Knoevenagel reaction by reacting malonic acid of formula $HOOC-CH_2-COOH$, on a lactol of the following formula (II):

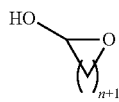
(II)

n being as defined above, in order to obtain a hydroxyacid of the following formula (I-1-bis):

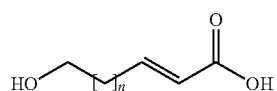
(I-1-bis)

wherein n is as defined above.

The present invention also relates to a method for preparing a compound of the following formula (I-1-ter):

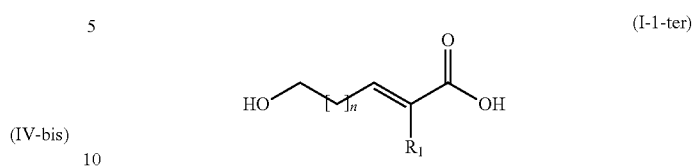
(I-1-ter)

wherein:

$R_1$ represents: H, F, Cl, Br, $CF_3$ or a linear or branched alkyl group comprising from 1 to 6 carbon atoms, said alkyl group being optionally substituted with a halogen atom; and n is greater than 4, said preparation method comprising:

the application of the Wittig-Horner reaction by reacting a phosphonate of the following formula (III-ter):

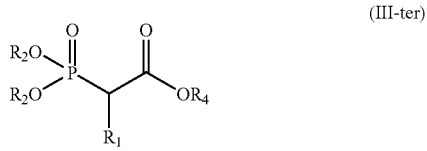
(III-ter)

wherein:

$R_1$ is as defined above, $R_2$ represents a linear or branched alkyl group, comprising from 1 to 6 carbon atoms, and preferably is an ethyl or methyl group, said $R_2$ groups may form a cycle with the oxygen atoms of the $OR_2$ groups and the phosphorus atom of the P=O group, and $R_4$ represents a linear or branched alkyl group comprising from 1 to 6 carbon atoms, and preferably is an ethyl group, on a lactol of the following formula (II):

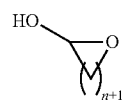
(II)

n being as defined above.

in order to obtain a hydroxyester of the following formula (IV-ter):

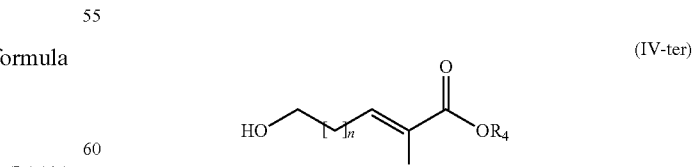
(IV-ter)

wherein n, $R_1$ and $R_4$ are as defined above.

and a reaction for saponifying the hydroxyester of the aforementioned formula (IV-ter), in order to obtain a hydroxyacid of the following formula (I-1-ter):

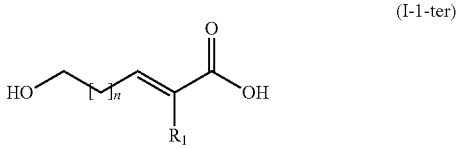

wherein n and $R_1$ are as defined above.

According to a preferred embodiment, the method of the invention as defined above is characterized in that the lactol of formula (II) is obtained by reduction of a lactone of the following formula (V):

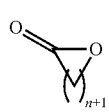

n being as defined above.

The step for partial reduction of the lactone (V) into a lactol of formula (II) is carried out in the presence of a reducing agent such as diisobutyl aluminium hydride. At the end of the reaction, the aluminium salts are removed by forming a water-soluble complex in the presence of Rozen salts or Rochelle salts (Reagents for organic synthesis, Vol. I, Louis Fieser and Mary Fieser, p. 36).

Advantageously, the reducing agents are selected from Dibal H (Posner Gary H. et al., 1991, *JOC*, 56(25), 6981-6987), Red A1, OMH1, tri(terbutoxy) aluminium lithium hydride (Mili Shokyo et al., 1990, *J. Chem. Soc. Perkin Trans.*, 1(4), 1228-1229) or any other aluminium hydride, the reactivity of which will have been curbed by introducing different groups.

According to another preferred embodiment, the method of the invention as defined above is characterized in that the lactone of formula (V) is obtained from a ketone of the following formula (VI), by applying the Baeyer-Villiger reaction:

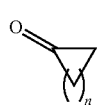

n being as defined above.

The Baeyer-Villiger reaction is notably described in the following articles: Friess SL, 1949, *JOC*, 71, 2571-2575, Kruizing a Wim H. et al., 1981, *JACS*, 103(17), 5183-5189).

Many techniques allowing oxidation of a ketone (VI) into a lactone (V) are known in the state of the art and may be used by one skilled in the art in this step. This oxidation requires the use of a solvent which may notably be methylene chloride, dichloro-1,2-ethane or any other inert chlorinated solvent. Experimental oxidation conditions may be mentioned, using 3-chloro-perbenzoic acid, as described in Ishihara et al., 1996, *J. Org. Chem.* 61, 4560-4567).

The present invention also relates to a method for preparing an unsaturated fatty hydroxyacid of the following formula (I-1):

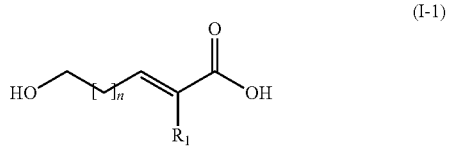

wherein:
$R_1$ represents: H, F, Cl, Br, $CF_3$ or a linear or branched alkyl group comprising from 1 to 6 carbon atoms, said alkyl group being optionally substituted with a halogen atom; and
n is greater than 4,
said preparation method comprising the following steps:
the reduction of a lactone of the following formula (V):

n being as defined above,
in order to obtain a lactol of the following formula (II):

n being as defined above,
the application of the Wittig-Horner reaction by reacting a phosphonate of the following formula (III):

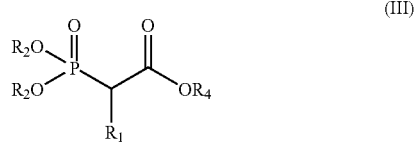

wherein:
$R_1$ is as defined above,
$R_2$ represents a linear or branched alkyl group, comprising from 1 to 6 carbon atoms, and preferably is an ethyl or methyl group, said $R_2$ groups may form a cycle with the oxygen atoms of the $OR_2$ groups and the phosphorus atom of the P=O group, and
$R_4$ represents a linear or branched alkyl group comprising from 1 to 6 carbon atoms, and preferably is an ethyl group,
or, when $R_1$=H, the application of the Doebner-Knoevenagel reaction by reacting a malonic acid derivative of formula $R_3OOC—CH_2—COOR_3$, $R_3$ being as defined above,
on the lactol of the aforementioned formula (II), in order to obtain a hydroxyester of the following formula (IV):

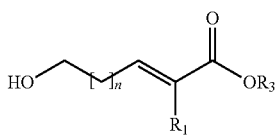
(IV)

wherein n, $R_1$ and $R_3$ are as defined above,
and, when $R_3$ represents an $R_4$ group as defined above, a reaction for saponifying the hydroxyester of the aforementioned formula (IV), in order to obtain a hydroxyacid of the aforementioned formula (I-1).

The present invention also relates to a method for preparing an unsaturated fatty hydroxy acid of the following formula (I-2):

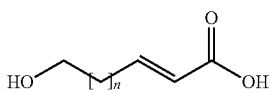
(I-2)

wherein n is greater than 4,
said preparation method comprising the following steps:
reducing a lactone of the following formula (V)

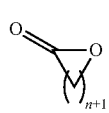
(V)

n being as defined above,
in order to obtain a lactol of the following formula (II):

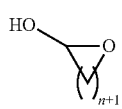
(II)

n being as defined above,
the application of the Wittig-Horner reaction by reacting a phosphonate of the following formula (III-2):

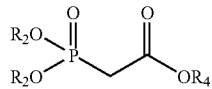
(III-2)

wherein:
$R_2$ represents a linear or branched alkyl group, comprising from 1 to 6 carbon atoms, and preferably is an ethyl or methyl group, said $R_2$ groups may form a cycle with the oxygen atoms of the $OR_2$ groups and the phosphorus atom of the P=O group, and
$R_4$ represents a linear or branched alkyl group comprising from 1 to 6 carbon atoms, and preferably is an ethyl group,
or the application of the Doebner-Knoevenagel reaction by reacting a malonic acid derivative of formula $R_3OOC—CH_2—COOR_3$, $R_3$ being as defined above, on the lactol of the aforementioned formula (II), in order to obtain a hydroxy ester of the following formula (IV-2):

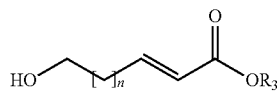
(IV-2)

wherein n and $R_3$ are as defined above,
and, when $R_3$ represents an $R_4$ group as defined above, a reaction for saponifying the hydroxy ester of the aforementioned formula (IV-2), in order to obtain a hydroxy acid of the aforementioned formula (I-2).

The compounds of formula (I-2) as defined above correspond to compounds of formula (I) wherein $R_3$ represents a hydrogen atom and $R_1$ represents a hydrogen atom.

The compounds of formula (III-2) as defined above correspond to compounds of formula (III) wherein $R_1$ represents a hydrogen atom.

The compounds of formula (IV-2) as defined above correspond to compounds of formula (IV) wherein $R_1$ represents a hydrogen atom.

The present invention also relates to a method for preparing an unsaturated fatty hydroxy acid of the following formula (I-2):

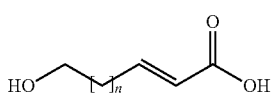
(I-2)

wherein n is greater than 4,
said preparation method comprising the following steps:
the reduction of a lactone of the following formula (V):

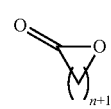
(V)

n being as defined above,
in order to obtain a lactol of the following formula (II):

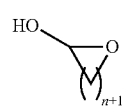
(II)

n being as defined above,
the application of the Wittig-Horner reaction by reacting a phosphonate of the following formula (III-2):

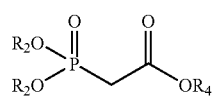
(III-2)

wherein:
R$_2$ represents a linear or branched alkyl group, comprising from 1 to 6 carbon atoms, and preferably is an ethyl or methyl group, said R$_2$ groups may form a cycle with the oxygen atoms of the OR$_2$ groups and the phosphorus atom of the P=O group, and R$_4$ represents a linear or branched alkyl group comprising from 1 to 6 carbon atoms, and preferably is an ethyl group, or the application of the Doebner-Knoevenagel reaction by reacting a malonic acid derivative of formula R$_4$OOC—CH$_2$—COOR$_4$, R$_4$ being as defined above, on the lactol of the aforementioned formula (II), in order to obtain a hydroxyester of the following formula (IV-2-bis):

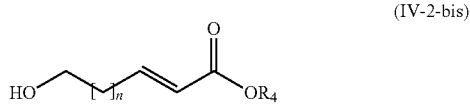

(IV-2-bis)

wherein n and R$_4$ are as defined above, and a reaction for saponifying the hydroxyester of the aforementioned formula (IV-2-bis), in order to obtain a hydroxyacid of the aforementioned formula (I-2).

The present invention also relates to a method for preparing an unsaturated fatty hydroxy acid of the following formula (I-3):

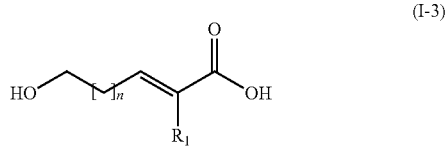

(I-3)

wherein:
R$_1$ represents: F, Cl, Br, CF$_3$ or a linear or branched alkyl group comprising from 1 to 6 carbon atoms, said alkyl group being optionally substituted with a halogen atom; and n is greater than 4, said preparation method comprising the following steps:
the reduction of a lactone of the following formula (V):

(V)

n being as defined above,
in order to obtain a lactol of the following formula (II):

(II)

n being as defined above,
the application of the Wittig-Horner reaction by reacting a phosphonate of the following formula (III-3):

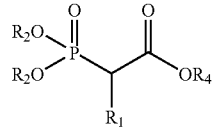

(III-3)

wherein:
R$_1$ is as defined above,

R$_2$ represents a linear or branched alkyl group, comprising from 1 to 6 carbon atoms, and preferably is a methyl group, said R$_2$ groups may form a cycle with the oxygen atoms of the OR$_2$ groups and the phosphorus atom of the P=O group, and R$_4$ represents a linear or branched alkyl group comprising from 1 to 6 carbon atoms, and preferably is an ethyl group, on the lactol of the aforementioned formula (II), in order to obtain a hydroxyester of the following formula (IV-3):

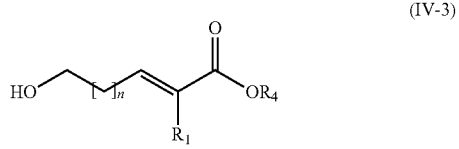

(IV-3)

wherein n, R$_1$ and R$_4$ are as defined above, and a reaction for saponifying the hydroxy ester of the aforementioned formula (IV-3) in order to obtain a hydroxy acid of the aforementioned formula (I-3).

The compounds of formula (I-3) as defined above correspond to compounds of formula (I) wherein R$_3$ represents a hydrogen atom and R$_1$ represents F, Cl, Br, CF$_3$ or an alkyl group.

The compounds of formula (III-3) as defined above correspond to compounds of formula (III) wherein R$_1$ represents F, Cl, Br, CF$_3$ or an alkyl group.

The compounds of formula (IV-3) as defined above correspond to compounds of formula (IV) wherein R$_1$ represents F, Cl, Br, CF$_3$ or an alkyl group.

An advantageous method according to the invention is a method as defined above, wherein n is larger than or equal to 6.

For the Wittig-Horner reaction, the working temperature is 40° C.: this reaction does not need a large supply of energy. As regards the Doebner-Knoevenagel reaction, the working temperature is 70° C., which therefore requires a more significant supply of energy. Both of these reactions are carried out in a basic medium with a deprotonation agent. Moreover, the Wittig-Horner reaction requires the presence of a secondary amine for the decarboxylation step.

An advantageous method according to the invention is a method as defined above where n is equal to 7, 8, 9, 10, 11, 12, 13 or 14.

The present invention also relates to the compounds as obtained by the method as defined above.

The present invention also relates to a cosmetic composition comprising a compound of the following formula (I-1):

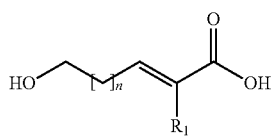

(I-1)

wherein:
R$_1$ represents: H, F, Cl, Br, CF$_3$ or a linear or branched alkyl group comprising from 1 to 6 carbon atoms, said alkyl group being optionally substituted with a halogen atom; and
n is greater than or equal to 7, notably greater than or equal to 8 and is preferably equal to 10, 13 or 14,
in association with a suitable carrier.

The present invention also relates to the use of a compound of the following formula (I-1):

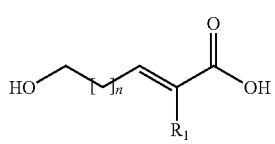

(I-1)

wherein:
R$_1$ represents: H, F, Cl, Br, CF$_3$ or a linear or branched alkyl group comprising from 1 to 6 carbon atoms, said alkyl group being optionally substituted with a halogen atom; and
n is greater than or equal to 7, notably greater than or equal to 8 and is preferably equal to 10, 13 or 14,
for preparing a cosmetic composition having anti-collagenase activity.

The present invention also relates to a compound of the following formula (I-2):

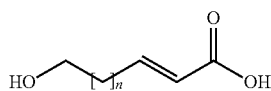

(I-2)

wherein n is equal to 10, 13 or 14.
Thus, the present invention relates to the following preferred compounds:

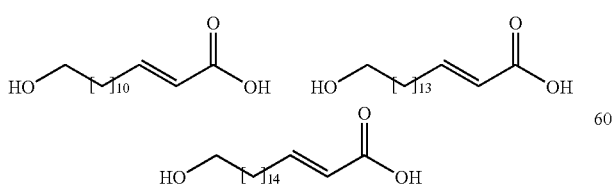

The present invention also relates to a cosmetic composition comprising a compound of formula (I-2) as defined above, in association with a suitable carrier.

The present invention also relates a cosmetic composition comprising a compound of formula

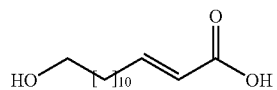

in association with a suitable carrier.
The present invention also relates a cosmetic composition comprising a compound of formula

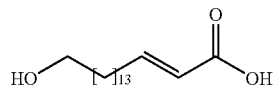

in association with a suitable carrier.
The present invention also relates a cosmetic composition comprising a compound of formula

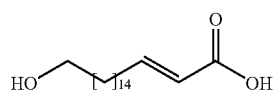

in association with a suitable carrier.
The present invention also relates to a compound of the following formula (I-3):

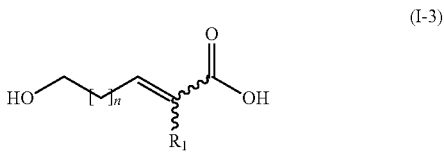

(I-3)

wherein:
R$_1$ represents: F, Cl, Br, CF$_3$ or a linear or branched alkyl group comprising from 1 to 6 carbon atoms, said alkyl group being optionally substituted with a halogen atom; and
n is greater than 4 and is notably equal to 6, 7, 8, 9, 10, 11, 12, 13 or 14,
said compound being in the form of Z or E stereoisomers or as a mixture of these different forms.

The compounds of formula (I-3) have the particularity of being less metabolizable and less lipophilic than the compounds of formula (I-2).

The present invention relates to a cosmetic composition comprising a compound as defined above, fitting formula (I-3) as defined above, in association with a suitable carrier.

EXAMPLE 1

Operating Procedure for DHA Synthesis

Obtaining the compound of formula (I-1) with R$_1$=H and n=6
1. Preparation of Oxonan-2-One
43.5 g (345 mmol) of cyclooctanone (compound of formula (VI) with n=6) (ACROS) are placed in solution in 430 ml of dichloroethane. 170 g (985 mmol) of meta-chloroperbenzoic acid are then added. The medium is heated to 80° C. for 48 hours. At room temperature, 400 ml of a Na$_2$S$_2$O$_5$ and NaHCO$_3$ saturated solution (1/1 v/v) are added. The medium is strongly stirred for 18 hours. The organic phase is separated and placed into the presence of KI and H$_2$O for 6 hours. The organic phase is separated and washed with a Na$_2$S$_2$O$_3$ saturated solution, with a NaCl saturated solution, and is then dried on MgSO$_4$, filtered and concentrated in vacuo in order to obtain 36 g of crude product.

The lactone is purified by trituration in pentane (60 ml), and then by filtration of the cold-formed meta-chlorobenzoic acid precipitate, m=26.6 g (54%).

The obtained lactone is a compound of formula (V) with n=6:

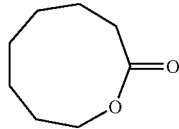

Characterization:
TLC: Rf=0.3 (heptane/ethyl acetate 7/3)
$^1$H NMR (300 MHz, CDCl$_3$): δ 1.42-1.49 (m, 4H); 1.65-1.75 (m, 6H); 2.30 (t, J=5.4 Hz, 2H); 4.30 (t, J=5.7 Hz, 2H).

2. Step for Partial Reduction into Lactol 26.6 g (187.2 mmol) of lactone obtained in the preceding step are diluted in 210 ml of toluene, under a nitrogen atmosphere. The medium is cooled to −78° C. and 156.4 ml (189.1 mmol) of Dibal-H (ACROS) in a 20% solution in toluene are added dropwise while maintaining the temperature at −78° C. The mixture is stirred for 2 hours at −78° C. 200 ml of a solution saturated with Rozen salts (double tartrate salts; ACROS) are added at −78° C. After 18 hours of strong stirring at room temperature, the biphasic mixture is filtered on celite, and then extracted with ethyl acetate. The organic phases are washed with a NaCl saturated solution, dried on MgSO$_4$, filtered and concentrated in vacuo in order to obtain 26 g of crude product (including 25% of diol derivative, i.e. an estimated yield of 72%). The lactol in an open form/cyclic form equilibrium is thus used, without additional purification.

The obtained lactol is a compound of formula (II) with n=6:

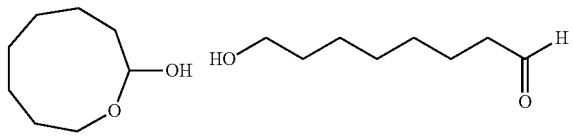

Characterization:
TLC: Rf=0.4 (heptane/ethyl acetate 6/4)
$^1$H NMR (300 MHz, CDCl$_3$): δ 1.34-1.68 (m, 10H); 2.45 (t, J=5.4 Hz, 2H); 3.66 (t, J=6.6 Hz, 2H); 9.78 (t, J=1.8 Hz, 1H).

3. Wittig-Horner Reaction 19 g (131.8 mmol) of lactol obtained in the preceding step are diluted in 250 ml of ethanol. 31.4 ml (158.1 mmol) of triethylphosphonoacetate (compound of formula (III) with R$_2$=R$_4$=Et and R$_1$=H) are added to the medium in presence of 27.3 g (197.5 mmol) of potassium carbonate. The reaction medium is heated to 40° C. for 18 hours. At room temperature, the medium is hydrolyzed by 200 ml of distilled water and extracted with ethyl acetate. The organic phases are washed with a NaCl saturated solution, dried on MgSO$_4$, filtered and concentrated in vacuo in order to obtain 20 g of crude product.

The obtained ester is purified by chromatography with (heptane/ethyl acetate 7/3) elution: 15 g of product are obtained (53% yield).

The obtained ester is a compound of formula (IV) with n=6, R$_1$=H and R$_4$=Et.

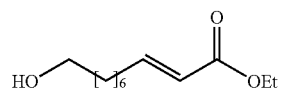

Characterization:
TLC: Rf=0.4 (heptane/ethyl acetate 7/3)
$^1$H NMR (300 MHz, CDCl$_3$): δ 1.24-1.38 (m, 9H); 1.43-1.50 (m, 2H); 1.51-1.57 (m, 2H); 2.15-2.21 (q, 2H); 3.60-3.64 (t, 2H); 4.14-4.20 (t, 2H); 5.77-5.82 (d, J=15.6 Hz, 1H); 6.91-6.98 (dt, J=15.6 Hz, 1H).

4. Saponification Reaction 0.60 g (2.81 mmol) of hydroxyester obtained in the preceding step are solubilized in 10 volumes of tetrahydrofurane. 3.4 ml (6.75 mmol) of a 2M soda solution are slowly added. The medium is heated to 65° C. for 3 hours. Once the reaction is completed, the medium is hydrolyzed by adding a 3M hydrochloric acid solution, until pH=2 is obtained. The mixture is dry-concentrated and the aqueous phase is then extracted with ethyl acetate. The organic phases are washed with a NaCl saturated solution, dried on MgSO$_4$, filtered and concentrated in vacuo in order to obtain 0.6 g of crude product.

The expected unsaturated hydroxyacid is obtained, as a white solid, by recrystallization from cold acetonitrile, m=0.37 g (71%).

The obtained hydroxy acid is a compound of formula (I-2) with n=6:

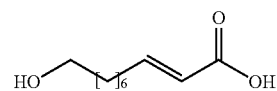

Characterization:
TLC: Rf=0.1 (heptane/ethyl acetate 6/4)
$^1$H NMR (300 MHz, CDCl$_3$): δ 1.33-1.37 (m, 6H); 1.45-1.49 (m, 2H); 1.55-1.58 (m, 2H); 2.20-2.25 (q, 2H); 3.62-3.66 (t, 2H); 5.79-5.84 (d, J=15.6 Hz, 1H); 7.03-7.10 (dt, J=15.6 Hz, 1H).
Mass spectroscopy: [M-Na]$^+$ 209 (calculated 186)
Melting point: 62.5° C.±1° C.

EXAMPLE 2

Operating Procedure for Synthesis of 10-hydroxy-dec-2-fluoro-2-enoic acid

Obtaining the compound of formula (I-3) with R$_1$=F and n=6

Only step 3 is modified (Wittig-Horner reaction): starting with the lactol (obtained in step 2 of Example 1) (0.89 g; 7.7 mmol), the Wittig-Horner reaction is conducted in the presence of methyldiethylphosphonofluoroacetate (compound of formula (III) with R$_2$=Et, R$_1$=F and R$_4$=Me) (2.1 g; 9.2 mmol) and potassium carbonate (1.6 g; 11.5 mmol) in ethanol (9 ml) at 40° C. Step 4 (saponification) is conducted according to the preceding procedure. The product obtained after recrystallization is in the form of a cis/trans mixture.

The obtained hydroxyacid is a compound of formula (I-3) with $R_1$=F and n=6:

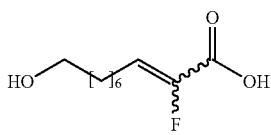

Characterization:
TLC: Rf=0.1 (heptane/ethyl acetate 6/4)
$^1$H NMR (300 MHz, CDCl$_3$): δ 1.36-1.62 (m, 20H); 2.27-2.30 (m, 2H, cis form); 2.50-2.58 (m, 2H, trans form); 3.69 (m, 4H); 6.05 (dt, J=21.6 Hz, 1H, trans form) and 6.25 (dt, J=40.8 Hz, 1H, cis form).
Mass spectroscopy: [M-Na]+ 227 (calculated 204)

EXAMPLE 3

Operating Procedure for Synthesis of 9-hydroxy-nona-2t-enoic acid

The synthesis procedure of Example 1 is applied to cycloheptanone (Aldrich) (compound of formula (VI) with n=5) in order to lead to 9-hydroxy-nona-2t-enoic acid, which is a compound of formula (I-2) with n=5:

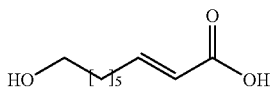

Characterization:
TLC: Rf=0.1 (heptane/ethyl acetate 6/4)
$^1$H NMR (300 MHz, CDCl$_3$): δ 1.36-1.61 (m, 8H); 2.22-2.27 (m, 2H); 3.67 (t, J=6.3 Hz, 2H); 5.84 (dt, J=15.6 Hz, 1H); 7.09 (dt, J=15.6 Hz, 1H).
Mass spectroscopy: [M-Na]$^+$ 195 (calculated 172)

EXAMPLE 4

Operating Procedure for Synthesis of 11-hydroxy-undeca-2t-enoic acid

The synthesis procedure of Example 1 is applied to cyclononanone (Aldrich) (compound of formula (VI) with n=7) in order to lead to 11-hydroxy-undeca-2t-enoic acid, which is a compound of formula (I-2) with n=7:

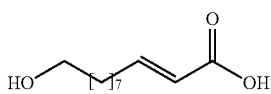

Characterization:
TLC: Rf=0.1 (heptane/ethyl acetate 6/4)
$^1$H NMR (300 MHz, CDCl$_3$): δ 1.33-1.61 (m, 12H); 2.20-2.28 (m, 2H); 3.66 (t, J=6.0 Hz, 2H); 5.84 (dt, J=15.9 Hz, 1H); 7.09 (dt, J=15.9 Hz, 1H).
Mass spectroscopy: [M-Na]$^+$ 223 (calculated 200)

EXAMPLE 5

Operating Procedure for Synthesis of 12-hydroxy-dodeca-2t-enoic acid

The synthesis procedure of Example 1 is applied to cyclodecanone (Aldrich) (compound of formula (VI) with n=8) in order to lead to 12-hydroxy-dodeca-2t-enoic acid, which is a compound of formula (I-2) with n=8:

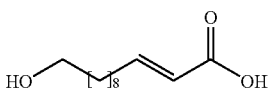

Characterization:
TLC: Rf=0.1 (heptane/ethyl acetate 6/4)
$^1$H NMR (300 MHz, CDCl$_3$): δ 1.35-1.56 (m, 14H); 2.20-2.27 (m, 2H); 3.55 (t, J=6.6 Hz, 2H); 5.80 (dt, J=15.6 Hz, 1H); 6.96 (dt, J=15.6 Hz, 1H).
Mass spectroscopy: [M-Na]$^+$ 237 (calculated 214).

EXAMPLE 6

Operating Procedure for Synthesis of 12-hydroxy-dodeca-2-fluoro-2t-enoic acid: ($R_1$=F, n=8)

The synthesis procedure of Example 2 is applied to cyclodecanone (Aldrich) (compound of formula (VI) with n=8) in order to lead, as a cis/trans mixture, to 12-hydroxy-dodeca-2-fluoro-2t-enoic acid, which is a compound of formula (I-3) with $R_1$=F and n=8:

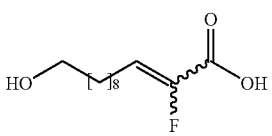

Characterization:
TLC: Rf=0.1 (heptane/ethyl acetate 6/4)
$^1$H NMR (300 MHz, CDCl$_3$): δ 1.34-1.56 (m, 14H); 2.24-2.27 (m, 2H, cis form) or 2.49-2.54 (m, 2H, trans structure); 3.55 (t, J=6.6 Hz, 2H); 5.97 (dt, J=21.9 Hz, 1H trans structure) or 6.10 (dt, J=55.2 Hz, 1H, cis form).
Mass spectroscopy: [M-Na]$^+$ 255 (calculated 232).

EXAMPLE 7

Operating Procedure for Synthesis of 13-hydroxy-tridec-2t-enoic acid

The synthesis procedure of Example 1 is applied to oxacyclododecan-2-one (Aldrich) (compound of formula (V) with n=9) in order to lead to 13-hydroxy-tridec-2t-enoic acid, which is a compound of formula (I-2) with n=9:

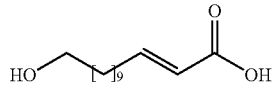

Characterization:
TLC: Rf=0.1 (heptane/ethyl acetate 6/4)
$^1$H NMR (300 MHz, CDCl$_3$): δ 1.27-1.63 (m, 16H); 2.21-2.28 (m, 2H); 3.64 (t, J=3.6 Hz, 2H); 5.84 (dt, J=15.6 Hz, 1H); 7.09 (dt, J=15.6 Hz, 1H).
Mass spectroscopy: [M-Na]$^+$ 251 (calculated 228)

EXAMPLE 8

Operating Procedure for Synthesis of 14-hydroxy-tetradec-2t-enoic acid

The synthesis procedure of Example 1 is applied to oxacyclotridecan-2-one (Aldrich) (compound of formula (V) with n=10) in order to lead to 14-hydroxy-tetradec-2t-enoic acid, which is a compound of formula (I-2) with n=10:

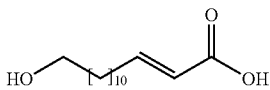

Characterization:
TLC: Rf=0.1 (heptane/ethyl acetate 6/4)
$^1$H NMR (300 MHz, CDCl$_3$): δ 1.29-1.35 (m, 14H); 1.46-1.61 (m, 4H); 2.21-2.29 (m, 2H); 3.66 (t, J=6.6 Hz, 2H); 5.84 (dt, J=1.5.6 Hz, 1H); 7.09 (dt, J=15.6 Hz, 1H).
Mass spectroscopy: [M-Na]$^+$ 265 (calculated 242)

EXAMPLE 9

Operating Procedure for Synthesis of 14-hydroxy-tetradec-2-fluoro-2-enoic acid

The synthesis procedure of Example 2 is applied to oxacyclotridecan-2-one (Aldrich) (compound of formula (V) with n=10) in order to lead, as a cis/trans mixture, to 14-hydroxy-tetradec-2-fluoro-2-enoic acid, which is a compound of formula (I-3) with R$_1$=F and n=10:

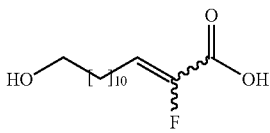

Characterization:
TLC: Rf=0.1 (heptane/ethyl acetate 6/4)
$^1$H NMR (300 MHz, CDCl$_3$): δ 1.29 (m, 28H); 1.42-1.62 (m, 8H); 2.27-2.31 (m, 2H, cis form); 2.51-2.56 (m, 2H, trans form); 3.68 (t, J=6.6 Hz, 2H); 3.70 (t, J=6.6 Hz, 2H); 6.04 (dt, J=21.3 Hz, 1H, trans form); 6.27 (dt, J=33.0 Hz, 1H, cis form).
Mass spectroscopy: [M-Na]$^+$ 283 (calculated 260)

EXAMPLE 10

Operating Procedure for Synthesis of 17-hydroxy-heptadec-2t-enoic acid

The synthesis procedure of Example 1 is applied to cyclopentadecanolide (Lancaster) (compound of formula (V) with n=13) in order to lead to 17-hydroxy-heptadec-2t-enoic acid, which is a compound of formula (I-2) with n=13:

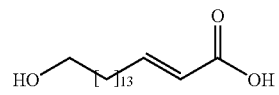

Characterization:
TLC: Rf=0.1 (heptane/ethyl acetate 6/4)
$^1$H NMR (300 MHz, CDCl$_3$): δ 1.27-1.32 (m, 20H); 1.46-1.61 (m, 4H); 2.20-2.29 (m, 2H); 3.67 (t, J=6.6 Hz, 2H); 5.84 (dt, J=15.6 Hz, 1H); 7.08 (dt, J=15.6 Hz, 1H).
Mass spectroscopy: [M-Na]$^+$ 307 (calculated 284)

EXAMPLE 11

Operating Procedure for Synthesis of 17-hydroxy-heptadec-2-fluoro-2-enoic acid

The synthesis procedure of Example 2 is applied to cyclopentadecanolide (Lancaster) (compound of formula (V) with n=13) in order to lead, as a cis/trans mixture, to 17-hydroxy-heptadec-2-fluoro-2-enoic acid, which is a compound of formula (I-3) with R$_1$=F and n=13:

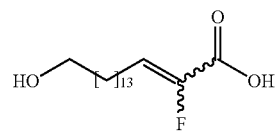

Characterization:
TLC: Rf=0.1 (heptane/ethyl acetate 6/4)
$^1$H NMR (300 MHz, CDCl$_3$): δ 1.27 (m, 40H); 1.45-1.62 (m, 8H); 2.24-2.32 (m, 2H, cis form); 2.50-2.58 (m, 2H, trans form); 3.69 (t, J=6.6 Hz, 4H); 6.05 (dt, J=21.6 Hz, 1H, trans form) and 6.26 (dt, J=40.8 Hz, 1H, cis form).
Mass spectroscopy: [M-H]$^-$ 301 (calculated 302)
Melting point: 77° C.±1° C.

EXAMPLE 12

Operating Procedure for Synthesis of 18-hydroxy-octadec-2t-enoic acid

The synthesis procedure of Example 1 is applied to cyclohexadecanolide (Lancaster) (compound of formula (V) with n=14) in order to lead to 18-hydroxy-octadec-2t-enoic acid (yield=72%), which is a compound of formula (I-2) with n=14:

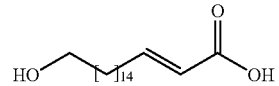

Characterization:

TLC: Rf=0.1 (heptane/ethyl acetate 6/4)

$^1$H NMR (300 MHz, CDCl$_3$): δ 1.27-1.65 (m, 26H); 2.19-2.39 (m, 2H) 3.67 (t, J=6.6 Hz, 2H); 5.83 (dt, J=15.6 Hz, 1H); 7.09 (dt, J=15.6 Hz, 1H).

Mass spectroscopy: [M-Na]$^+$ 321 (calculated 298)

EXAMPLE 13

Doener-Knovenagel Reaction from Oxacyclotridecanol

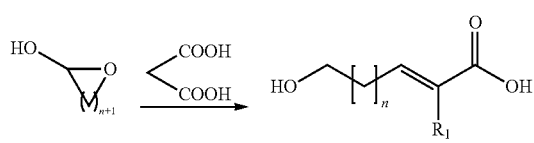

1.4 g (7.0 mmol) of oxacyclotridecanol obtained according to the procedure of partial reduction into lactol (lactol of formula (II) with n=13) are placed in solution, under a flow of nitrogen, in 4 volumes of pyridine, in the presence of 1.09 g (10.5 mmol) of malonic acid and 0.11 ml of piperidine. The reaction medium is heated to 80° C. for 1 hr 30 min, and then refluxed for 2 hours. At room temperature, the solution is poured onto a 3M HCl solution (50 ml). The filtered solid is washed with water and then recystallized from acetonitrile (1.2 g obtained, i.e. 70% yield).

EXAMPLE 14

Operating Procedure for Synthesis of 18-hydroxy-octadec-2-fluoro-2t-enoic acid

The synthesis procedure of Example 1 is applied to cyclohexadecanolide (Lancaster) (compound of formula (V) with n=14) in order to lead to 18-hydroxy-octadec-2-fluoro-2t-enoic acid (yield=73%), which is a compound of formula (I-2) with n=14:

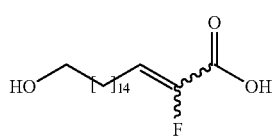

Characterization:

TLC: Rf=0.1 (heptane/ethyl acetate 6/4)

$^1$H NMR (300 MHz, CDCl$_3$): δ 1.28-1.62 (m, 52H); 2.28-2.31 (m, 2H, cis form); 2.54-2.56 (m, 2H, trans form); 3.69 (t, J=6.6 Hz, 4H); 6.07 (dt, J=21.6 Hz, 1H, trans form); 6.30 (dt, J=33.0 Hz, 1H, cis form).

Mass spectroscopy: [M-Na]$^+$ 339 (calculated 316)

EXAMPLE 15

Characterization of 15-hydroxy-pentadec-2t-enoic acid

The synthesis procedure of Example 1 is applied to a compound of formula (V) with n=11 in order to lead to 15-hydroxy-pentadec-2t-enoic acid, which is a compound of formula (I-2) with n=11:

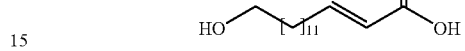

TLC: Rf=0.1 (heptane/ethyl acetate 6/4)

$^1$H NMR (300 MHz, CDCl$_3$): δ 1.28-1.60 (m, 20H); 2.21-2.28 (m, 2H); 3.66 (t, J=6.6 Hz, 2H); 5.83 (dt, J=15.6 Hz, 1H); 7.09 (dt, J=15.6 Hz, 1H).

Mass spectroscopy: [M-Na]$^+$ 279 (calculated 256)

EXAMPLE 16

Characterization of 16-hydroxy-hexadec-2t-enoic acid

The synthesis procedure of Example 1 is applied to a compound of formula (V) with n=12 in order to lead to 15-hydroxy-hexadec-2t-enoic acid, which is a compound of formula (I-2) with n=12:

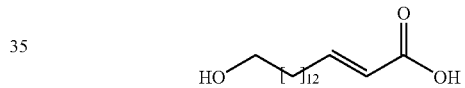

TLC: Rf=0.1 (heptane/ethyl acetate 6/4)

$^1$H NMR (300 MHz, CDCl$_3$): δ 1.28-1.61 (m, 22H); 2.21-2.28 (m, 2H); 3.66 (t, J=6.6 Hz, 2H); 5.85 (dt, J=15.0 Hz, 1H); 7.09 (dt, J=15.6 Hz, 1H).

Mass spectroscopy: [M-Na]$^+$ 293 (calculated 270).

The invention claimed is:

1. A method for preparing a compound of the following formula (I):

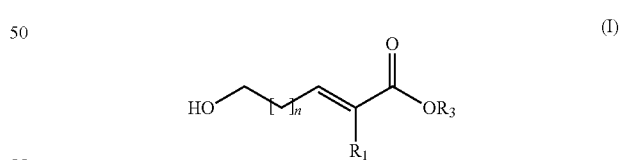

wherein:
 R$_3$ represents H or a linear or branched R$_4$ alkyl group comprising 1 to 6 carbon atoms,
 R$_1$ represents: H, F, Cl, Br, CF$_3$ or a linear or branched alkyl group comprising from 1 to 6 carbon atoms, said alkyl group being optionally substituted with a halogen atom; and
 n is greater than 4,
said preparation method comprising:
 the application of the Wittig-Horner reaction by reacting a phosphonate of the following formula (III):

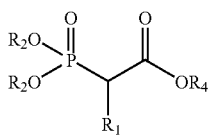

(III)

wherein:
$R_1$ is as defined above,
$R_2$ represents a linear or branched alkyl group, comprising from 1 to 6 carbon atoms, said $R_2$ groups may form a cyclic group with the oxygen atoms of the $OR_2$ groups and the phosphorus atom of the P=O group, and
$R_4$ represents a linear or branched alkyl group, comprising from 1 to 6 carbon atoms,
or, when $R_1$=H, the application of the Doebner-Knoevenagel reaction by reacting a malonic acid derivative of formula $R_3OOC—CH_2—COOR_3$, $R_3$ being as defined above, on a lactol of the following formula (II):

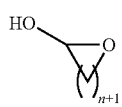

(II)

n being as defined above,
in order to obtain a hydroxyester of the following formula (IV):

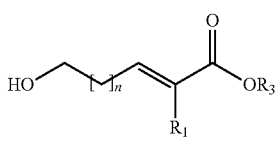

(IV)

wherein n, $R_3$ and $R_1$ are as defined above,
and optionally, when $R_3$ represents a group $R_4$ as defined above, a reaction for saponifying the hydroxyester of the aforementioned formula (IV) in order to obtain a hydroxyacid of the following formula (I):

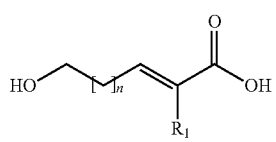

(I)

wherein n and $R_1$ are as defined above.

2. The method according to claim 1, wherein the lactol of formula (II) is obtained by reduction of a lactone of the following formula (V):

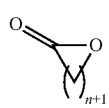

(V)

n being as defined in claim 1.

3. The method according to claim 2, wherein the lactone of formula (V) is obtained from a ketone of the following formula (VI), by applying the Baeyer-Villiger reaction:

(VI)

wherein n is greater than 4.

4. A method for preparing an unsaturated fatty hydroxyacid of the following formula (I-1):

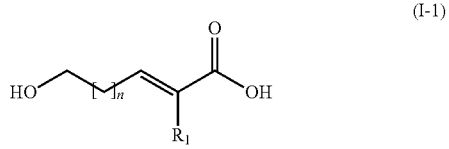

(I-1)

wherein:
$R_1$ represents: H, F, Cl, Br, $CF_3$ or a linear or branched alkyl group comprising from 1 to 6 carbon atoms, said alkyl group being optionally substituted with a halogen atom; and
n is greater than 4,
said preparation method comprising the following steps:
the reduction of a lactone of the following formula (V):

(V)

n being as defined above,
in order to obtain a lactol of the following formula (II):

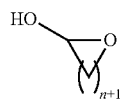

(II)

n being as defined above,
the application of the Wittig-Horner reaction by reacting a phosphonate of the following formula (III):

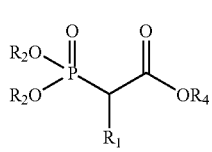

(III)

wherein:
$R_1$ is as defined above,
$R_2$ represents a linear or branched alkyl group, comprising from 1 to 6 carbon atoms, said $R_2$ groups may form a cycle with the oxygen atoms of the $OR_2$ groups and the phosphorus atom of the P=O group, and $R_4$ represents a linear or branched alkyl group comprising from 1 to 6 carbon atoms, or, when $R_1$=H, the application of the Doebner-Knoevenagel reaction by reacting a malonic acid derivative of formula $R_3OOC$—$CH_2$—$COOR_3$, $R_3$ being as defined above, on the lactol of the aforementioned formula (II), in order to obtain a hydroxyester of the following formula (IV):

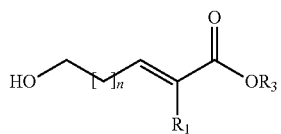

(IV)

wherein n, $R_1$ and $R_3$ are as defined above, and, when $R_3$ represents an $R_4$ group as defined above, a reaction for saponifying the hydroxyester of the aforementioned formula (IV), in order to obtain a hydroxy acid of the aforementioned formula (I-1).

5. The method according to claim 1, wherein n is greater than or equal to 6.

6. A compound of formula (I) as obtained according to the method as defined according to claim 1, wherein $R_1$ represents H and n is greater than or equal to 8.

7. A compound of the following formula (I-3):

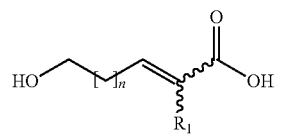

(I-3)

wherein:

$R_1$ represents: F, Cl, Br, $CF_3$ or a linear or branched alkyl group comprising from 1 to 6 carbon atoms, said alkyl group being optionally substituted with a halogen atom; and n is equal to 7, 8, 9, 10, 11, 12, 13 or 14, said compound being in the form of Z or E stereoisomers or as a mixture of these different forms.

8. A compound of formula (I-3):

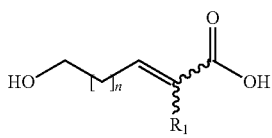

(I-3)

wherein:

$R_1$ represents: H, and n is greater than or equal to 8, said compound being in the form of Z or E stereoisomers or as a mixture of these different forms.

9. The method according to claim 1, wherein $R_2$ is an ethyl or methyl group.

10. The method according to claim 4, wherein $R_2$ is an ethyl or methyl group.

11. The method according to claim 1, wherein $R_4$ is an ethyl group.

12. The method according to claim 4, wherein $R_4$ is an ethyl group.

* * * * *